United States Patent [19]
Svetliza et al.

[11] Patent Number: 5,966,196
[45] Date of Patent: Oct. 12, 1999

[54] WIDE ANGLE APPARATUS FOR EXAMINATION OF THE EYE

[75] Inventors: Eduardo Svetliza, 5 Yigal Yadin Street, Ra'anana 43589; Dov Freiman, Rehovot; Zvi Paltiel, Ness Ziona, all of Israel

[73] Assignee: Eduardo Svetliza, Ra'Anana, Israel

[21] Appl. No.: 09/020,397

[22] Filed: Feb. 9, 1998

[30] Foreign Application Priority Data

Feb. 9, 1997 [IL] Israel .......................................... 120185

[51] Int. Cl.⁶ ......................................................... A61B 3/10
[52] U.S. Cl. ........................................... 351/205; 351/221
[58] Field of Search .................................... 351/205, 206, 351/221, 224; 396/18

[56] References Cited

U.S. PATENT DOCUMENTS 4,200,362  4/1980  Pomerantzeff et al. .
4,222,634  9/1980  Muchel .
5,007,729  4/1991  Erickson et al. .
5,054,906  10/1991 Lyons, Jr. .
5,125,730  6/1992  Taylor et al. .

OTHER PUBLICATIONS

K.R. Wilhelmus, M.D.; "Irrigating Eyelid Speculum"; American Journal of Ophthalmology, vol. 96, No. 4; Oct. 1983; pp. 549–550.

Commercial Publications: Massie Research Laboratories, 8 pages and Chromos Imaging, Incorporated 1993, 4 pages.

*Primary Examiner*—George Manuel
*Attorney, Agent, or Firm*—Needle & Rosenberg, P.C.

[57] ABSTRACT

Apparatus for wide angle examination of the eye fundus is provided. The apparatus includes an optical module providing a wide angle view image of the eye fundus and an image capturing unit connected to the optical module for capturing the wide angle view image. According to one aspect of the invention, the optical module includes a front lens complex for providing a primary large scale image of the fundus and an optical relay, connected to the front lens complex, for transforming the primary large scale image into a small scale image.

13 Claims, 5 Drawing Sheets

WIDE ANGLE APPARATUS FOR EXAMINATION OF THE EYE

FIELD OF THE INVENTION

The present invention relates to wide angle apparatus for examination of the eye.

BACKGROUND OF THE INVENTION

Apparatus for examining the eye are known in the art. The apparatus generally include a lens imaging module and a light sensitive apparatus, An example for such apparatus is the portable dynamic fundus instrument disclosed in U.S. Pat. No. 5,125,730 to Geraid et al.

This apparatus includes a video camera with an aspherical lens imaging module, designed to examine fundus blood vessels. One disadvantage of such apparatus is that they are incapable of covering a wide angle view of the fundus. Another disadvantage comes from their large physical dimensions which make the apparatus unsuitable for examining small eyes such as the eyes of a neonate and its retinal periphery. The original design of the optical unit uses a film camera technique.

Conventional wide angle optical units provide a wide angle view of the eye through an opening of the pupil of more than 2 mm in diameter. Such an opening can be achieved using special chemicals in the form of eye drops.

U.S. Pat. No. 5,007,729 discloses a wide angle ophthalmic lens utilizing aspherical optics, which is expensive and difficult to manufacture. Furthermore, this lens provides a curved imaging surface which is unsuitable for photographic purposes.

All of these apparatus require illumination. It will be appreciated that prior art illumination units are considerably large and require placing the examined eye in a fixed position, as disclosed in U.S. Pat. No. 4,200,362 to O. Pomerantzeff et al, for an ophthalmoscope with uniform illumination.

SUMMARY OF THE PRESENT INVENTION

It is an object of the present invention to provide a novel wide angle eye examination apparatus which overcomes the disadvantages of the prior art.

It is a further object of the present invention to provide a novel eye examination apparatus which does not include aspherical elements.

It is yet a further object of the present invention to provide apparatus which is small, and portable.

Yet another object of the present invention is to provide a portable illumination unit for use with the apparatus of the invention.

According to the present invention there is thus provided an apparatus for wide angle examination of the eye fundus including an optical module providing a wide angle view image of the eye fundus and an image capturing unit connected to the optical module for capturing the wide angle view image.

The image capturing unit is selected from the group consisting of a photographic camera, a video camera and a CCD.

According to one aspect of the invention, the optical module includes a front lens complex for providing a primary large scale image of the fundus and an optical relay, connected to the front lens complex, for transforming the primary large scale image into a small scale image.

The apparatus may also include an aberration correction optical complex, connected to the optical relay, for correcting color aberration and straitening curvature of the small scale image.

Another element which may be added to the apparatus of the invention is a rear lens complex, connected to the aberration correction optical complex, for imaging the small scale image on a predetermined plain.

According to a preferred embodiment of the invention, the apparatus also includes an illuminating unit, which is located around the optical module. The illumination unit can be a direct illumination unit, illuminating the eye through the pupil, or an indirect illumination unit, illuminating the eye through the eye globe.

An indirect illumination unit according to the invention may include a light source connected to a plurality of light guiding elements, the light guiding elements forming a hollow cylinder. The light guiding elements are slightly bent at the vicinity of the examined eye so as to adapt to the curved surface of the examined eye. The indirect illumination unit according to the invention may also include a circumferencial ring connected to the end of each the light guiding elements.

According to another aspect of the invention, the indirect illuminating unit includes a plurality of light sources and a circumferencial ring, having a tangential cross-section. The plurality of light sources being mounted on the periphery of the circumferencial ring.

According to the present invention there is also provided an apparatus for wide angle examination of the eye fundus including an optical module providing a wide angle view image of the eye fundus, an image capturing unit connected to the optical module for capturing the wide angle view image and an optical fiber unit connected between the optical module and the image capturing unit.

According to another aspect of the invention, the optical module includes a front lens complex for providing a primary large scale image of the fundus and an optic fiber CCD coupler, connected to the front lens complex, for transforming the primary large scale image into a small scale image.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

According to the present invention there is provided an optical module which is adapted to project the image of a wide angle view of an object into a small scale imaging plain.

Figure 1:
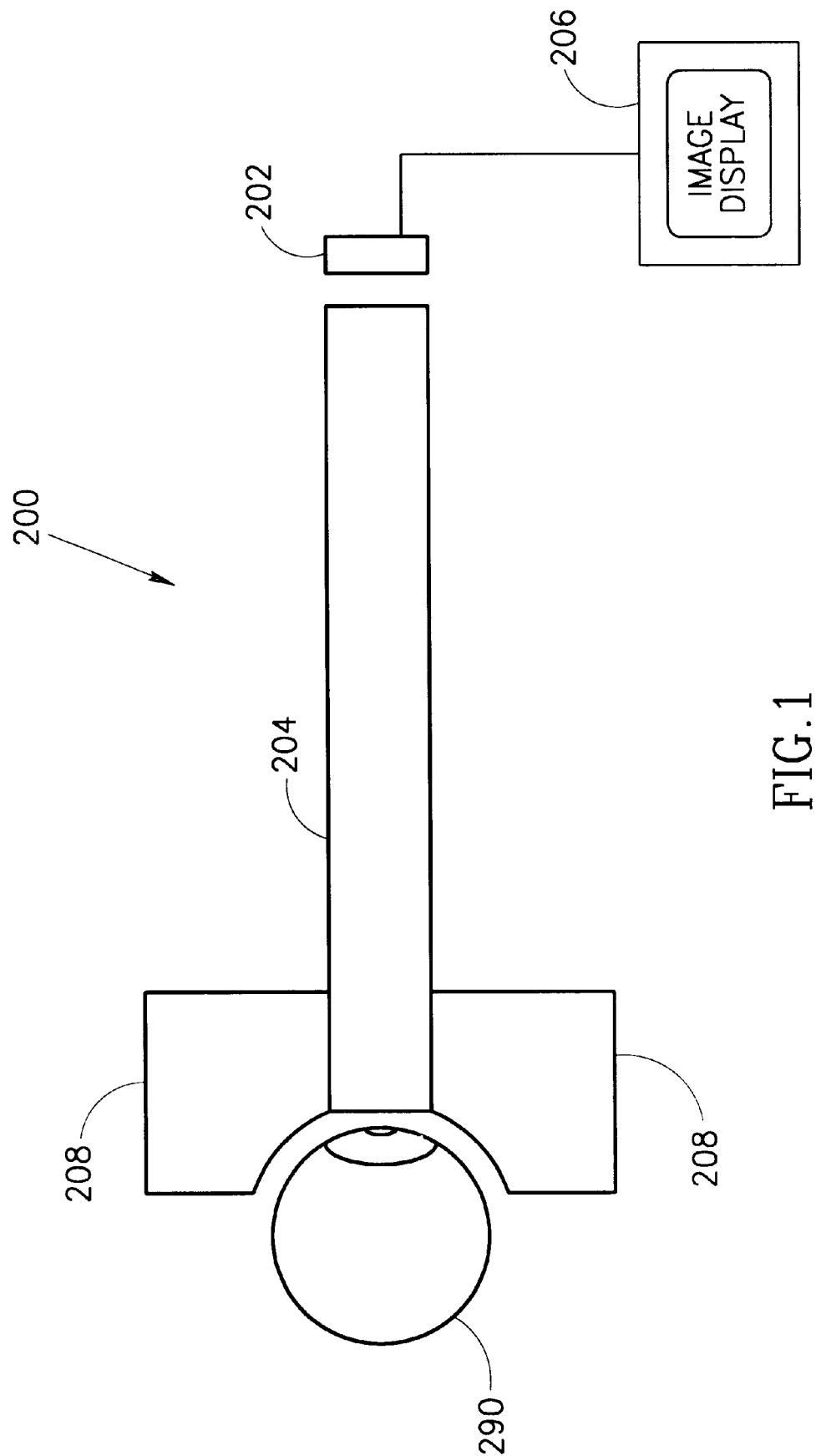
FIG. 1 is a partially pictorial, partially schematic illustration of an eye and apparatus for wide angle examination of the eye, constructed and operative in accordance with a preferred embodiment of the invention.
Figure 2:
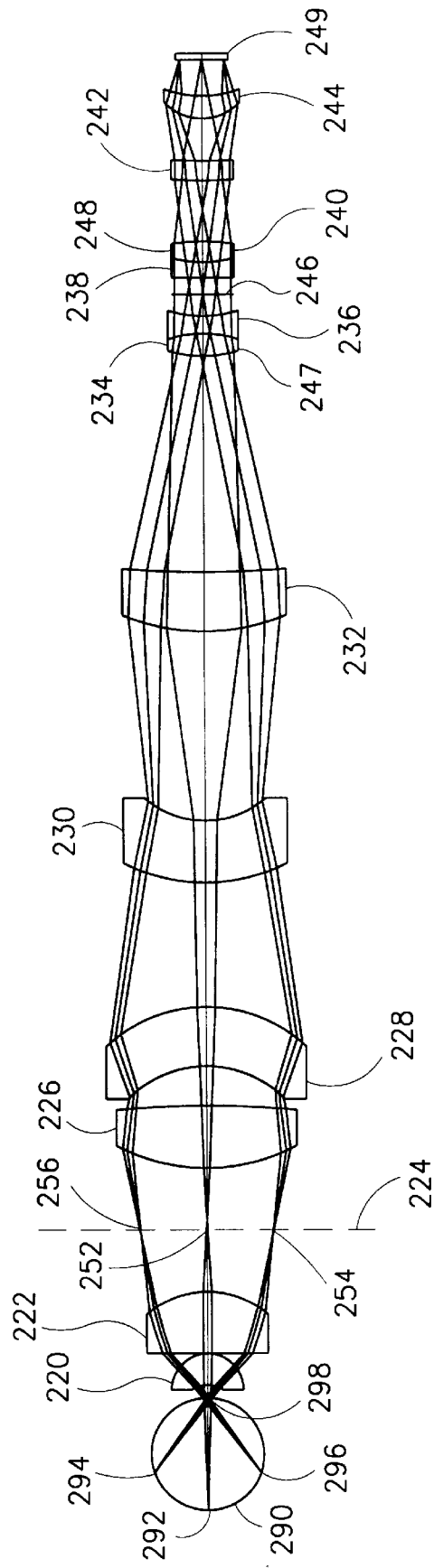
FIG. 2 is a schematic illustration in detail of the optical imaging module of the apparatus of FIG. 1.

Reference is now made to FIGS. 1 and 2. FIG. 1 is a partially pictorial, partially schematic illustration of an eye and apparatus for wide angle examination of the eye, generally designated 200, constructed and operative in accordance with a preferred embodiment of the invention. FIG. 2 is a schematic illustration in detail of the optical imaging module of apparatus 200.

Apparatus 200 includes an optical imaging module 204 and an image capturing element 202, such as charge coupled device (CCD), which is connected to a display apparatus 206. It is noted that display apparatus 206 may include means for image analysis and data storage, such as optical, magnetic or magneto-optic storage media, for storing the image provided by the image capturing element 202, a printer and the like.

Optical imaging module 204 is brought to close proximity or into contact with an eye 290 to be examined. The apparatus 200 also includes an illuminating unit 208, providing indirect illumination, through the sclera. It is noted that image capturing element 202 can be a photographic camera, a cathode ray tube (CRT), a CCD and the like.

The optical imaging module 204 includes a plurality of lenses 220, 222, 226, 228, 230, 232, 234, 236, 238, 240, 242 and 244. Lenses 220 and 222 form a front optical complex which generates a first image of the eye reticulum on a plane 224. Points 252, 254 and 256 are the images of points 292, 294 and 296 correspondingly. According to the present example, the front optical complex is divided into two lenses by way of convenience, while it will be appreciated that it may be implemented by a single lens or more than two lenses. This front optical complex provides a wide angle view of the eye fundus even through an undilated, 2 mm wide, pupil.

It will be appreciated that the radius of curvature of the front curved plane of lens 220 is similar to the radius of curvature of the tested eye. According to the invention, lens 220 can be replaced so as to adapt the apparatus 200 to various eye sizes.

Lenses 226, 228, 230, 232, 234, 236, 238, 240, 242 and 244 form an image relay which transforms the image generated by the front optical complex on plain 224 into a small scale imaging plain 249, suitable for projecting onto a conventional CCD detector.

Lens 226 combined with lens 228, form a field lens complex, which image the pupil in a converging manner. These lenses re-image the eye iris into plain 246, which acts as an aperture stop. The field lens complex also performs a correction of any slight curvature of plain 224.

Lens 230 combined with lens 232, form a lens complex which performs aberration correction.

Lenses 234, 236, 238, 240, 242, and 244 form a focusing complex.

Lenses 234 and 236 form a first lens doublet 247 and lenses 238 and 240 form a second lens doublet 248. These lens doublets perform correction of color aberration of the optical system.

Lenses 242 and 244 are singlet focusing lenses which perform focusing of the final image on plain 249, which is the location of the CCD 202.

According to a preferred embodiment of the present invention, the parameters which characterize the lenses of the apparatus 200 are as follows:

| LENS NO. | R1 (MM) | | R2 (MM) | | CT (MM) | GLASS TYPE |
|---|---|---|---|---|---|---|
| 220 | 7.00 | concave | 7.24 | convex | 6.30 | BK7 |
| 222 | 305.55 | convex | 22.77 | convex | 12.00 | SF15 |
| 226 | 41.40 | convex | 295.10 | convex | 12.00 | SF15 |
| 228 | 22.77 | concave | 28.59 | convex | 11.94 | SF15 |
| 230 | 36.65 | convex | 19.04 | concave | 12.00 | BK7 |
| 232 | 41.29 | convex | 295.10 | concave | 12.00 | LAF22 |
| 234 | 16.16 | convex | 14.69 | convex | 5.00 | SK2 |
| 236 | 14.69 | concave | 13.13 | concave | 3.00 | SF8 |
| 238 | 102.13 | concave | 16.35 | concave | 3.00 | SF2 |
| 240 | 16.35 | convex | 29.91 | convex | 5.00 | LAF2 |
| 242 | 56.56 | convex | 59.82 | concave | 4.00 | LAF22 |
| 244 | 10.86 | convex | 16.98 | concave | 4.85 | LAF22 | wherein,

R1 is a first radius of a given lens;

R2 is a second radius of a given lens; and

CT is the Center Thickness of the lens, i.e. the distance length between two centers of a given lens.

According to the invention, each of the lenses can be coated by various coatings such as an anti-reflective coating and the like.

It will be appreciated to those skilled in the art that since a spherical lens is considered a private case of an aspherical lens, it is also possible to provide a lens imaging module according to the invention, which consists of at least one aspherical element. Furthermore, the various dimensions of the above lenses may change when using different transparent materials such as special glass, plastic and the like.

Apparatus 200 is a relatively small, portable and easy to use examining tool, which allows performing tests on a variety of eye sizes from adult to premature neonates. The invention provides apparatus 200 as a hand held unit which can be used without fastening the patient's head in order to fixate the location of the examined eye.

Figure 3A:
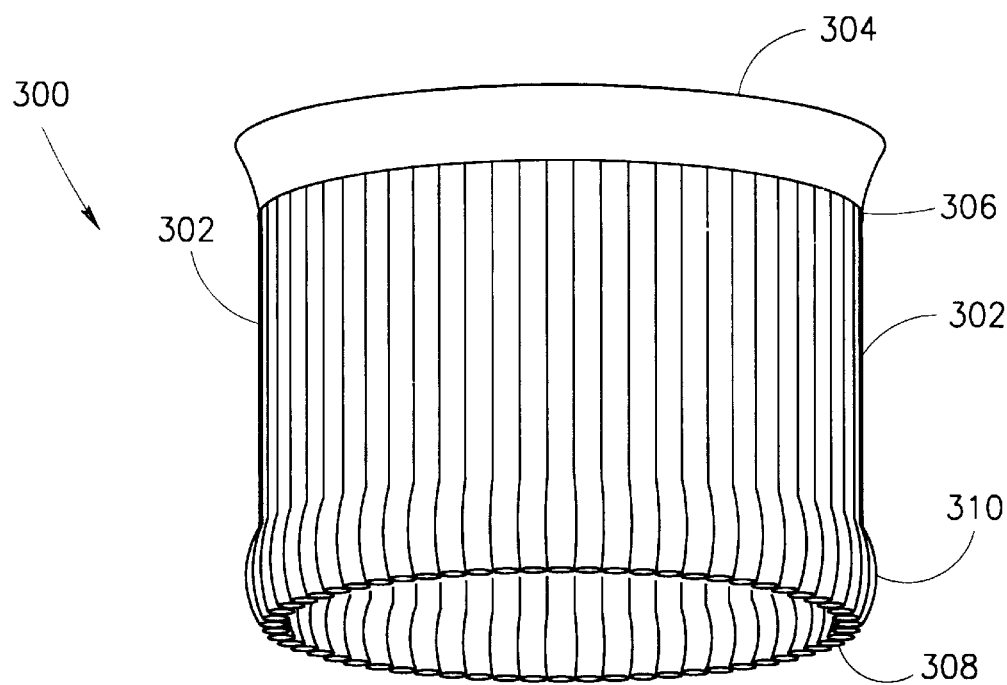
FIG. 3A is a schematic illustration of an illumination unit, constructed and no operative in accordance with another preferred embodiment of the present invention.
Figure 3B:
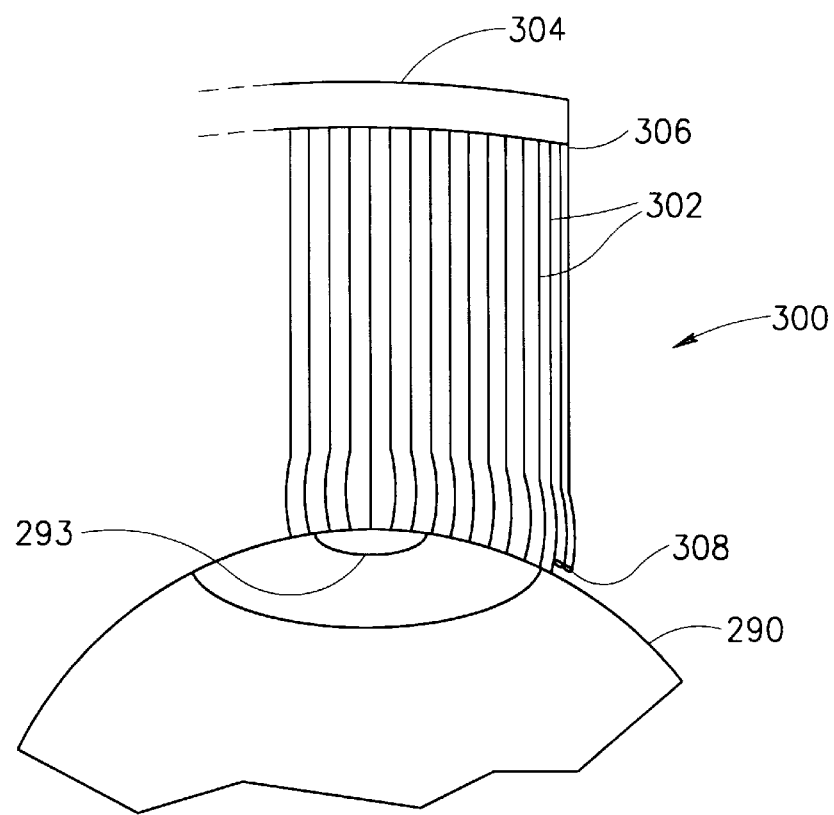
FIG. 3B is a partially schematic, partially pictorial illustration of an eye and of the illumination unit of FIG. 3A.

Reference is now made to FIGS. 3A and 3B. FIG. 3A is a schematic illustration of an illumination unit, generally referenced 300, constructed and operative in accordance with another preferred embodiment of the present invention. FIG. 3B is a partially schematic, partially pictorial illustration of an eye and of illumination unit 300.

Illumination unit 300 includes a light source 304 connected to a plurality of light guiding elements, generally designated, 302. The light guiding elements 302 are circumferencially arranged and act as light conduits, capable of transferring light from a first end 306 to the second end 308. Each of the light guiding elements 302 is slightly bent in the vicinity of the second end 308 according to the curvature of the globe of the examined eye 290.

According to one aspect of the invention, the light source 304 includes a plurality of controllable light source wherein, each of these light sources is directed towards a respective light guide. The light sources can be controlled either by gradually turning it on or of, or by placing a light valve between each light source and the respective light guide.

According to the present embodiment, illuminating unit 300 illuminates the eye from beyond the pupil area, providing indirect illumination through the sclera. The illumination unit 300 also provides partial illumination by separate control of some or all of the light sources of lighting unit 304.

Illuminating unit 300 is constructed as a generally hollow cylinder for mounting on apparatus 200 (FIG. 1). Thus, illuminating unit 300 is adapted to replace illuminating unit 208. Light guiding elements 302 are generally optic fibers. Illumination unit 300 permits illumination of an eye with an undilated pupil, which can be adapted to various eye sizes.

Figure 3C:
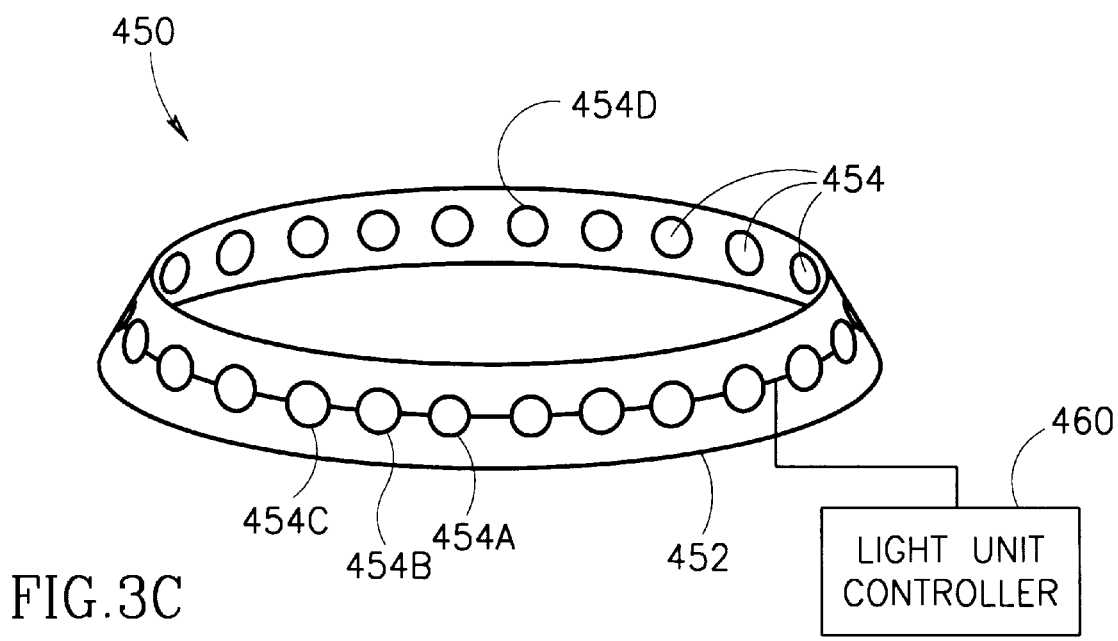
FIG. 3C is a schematic illustration of an illumination unit, constructed and operative in accordance with another preferred embodiment of the present invention.

Reference is now made to FIG. 3C which is a schematic illustration of an illumination unit, generally referenced 450, constructed and operative in accordance with another preferred embodiment of the present invention.

Illumination unit 450 includes a support ring 452 and a plurality of light sources 454A, 454B, 454C and 454D. in the present example, light source generally referenced 454 individually referenced by a sufix A, B, C, for example 454D is a variable wave-length light source which provides illumination at several predetermined wave-lengths. Each of the light sources 454 faces a tangential surface defined by the contact point between the illuminating unit 450 and the examined eye (not shown). The light sources 454 are connected to a controller 460 which provides control over the light intensity and the light distribution.

The illumination unit 450 is adapted to provide several modes of illumination. According to one mode of illumination, all of the light sources 454 are turned on so as to provide an even illumination of the examined eye fundus.

According to another mode of illumination, a selected group which include light sources 454A, 454B, and 454C is turned on, while the rest of the light sources 454 are turned off, thereby illuminating the examined eye from a selected angle.

According to a further mode, light source 454D, is turned on so as to produce illumination at a predetermined wave length. This mode Is suitable for examinations at Ultra-Violet light, Infra-Red light and the like.

Figure 4:
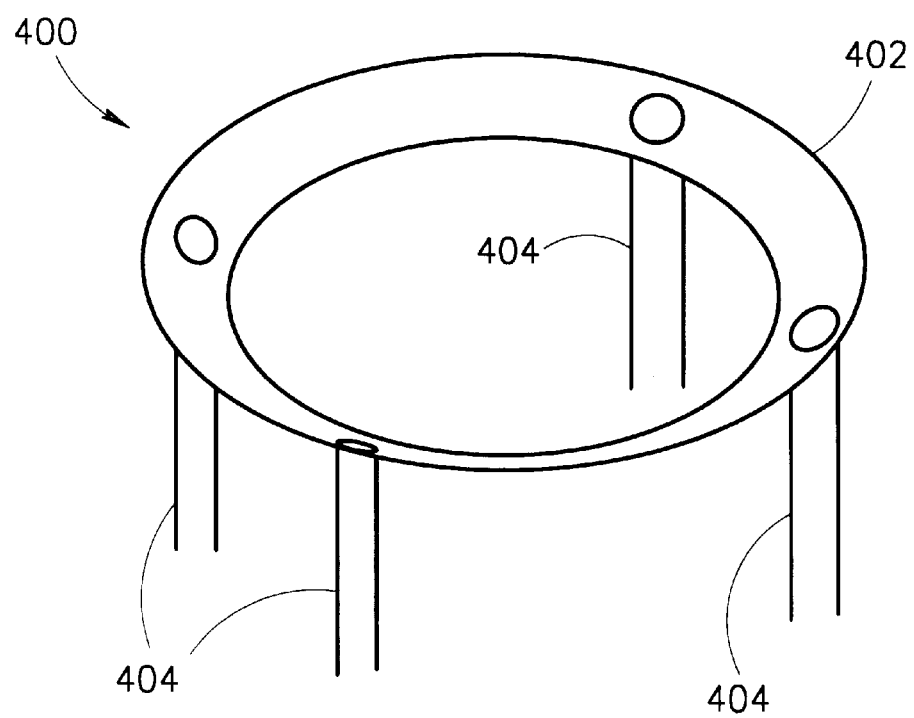
FIG. 4 which is a schematic illustration of an illumination unit, constructed and operative in accordance with a further preferred embodiment of the present invention.

Reference is now made to FIG. 4 which is a schematic illustration of an illumination unit, generally referenced 400, constructed and operative in accordance with a further preferred embodiment of the present invention.

Illuminating unit 400 includes a ring 402 and a plurality of light guiding elements 404. Light guiding elements 404 are generally optic-fibers which are used to conduct light from a light source to the eye. According to the present embodiment, the diameter of ring 402 is similar to the diameter of the pupil of the examined eye. Thus, the illuminating unit 400 can illuminates the examined eye directly through the opened pupil.

Illuminating unit 400 is constructed as a ring for mounting on apparatus 200 (FIG. 1). Thus illuminating unit 400 is also adapted to replace illuminating unit 208.

Figure 5:
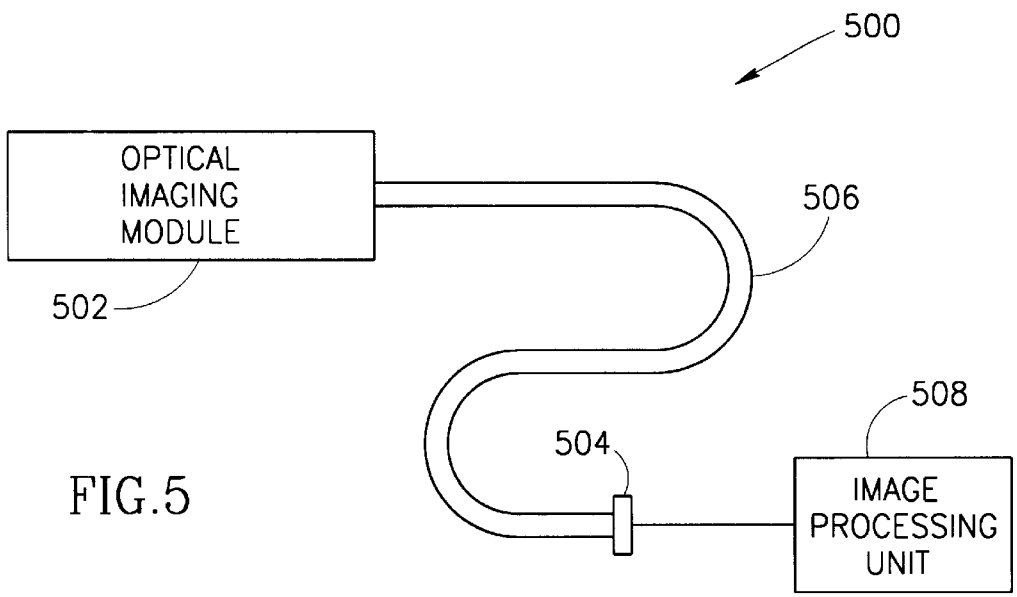
FIG. 5 is a partially pictorial, partially schematic illustration of an apparatus for wide angle examination of the eye, constructed and operative in accordance with a further preferred embodiment of the invention.

Reference is now made to FIG. 5 which is a partially pictorial, partially schematic illustration of an apparatus for wide angle examination of the eye, generally designated 500, constructed and operative in accordance with a further preferred embodiment of the invention.

Apparatus 500 includes an optical imaging module 502, an optical fiber unit 506 and an image capturing element 504. Optical fiber unit 506 includes a plurality of optical fibers. Image capturing element 504 is a charge coupled device (CCD), which is connected to an image processing unit 508.

Optical fiber unit 506 is connected to optical imaging module 502 at one end and to image capturing element 504, at the other end. The optical imaging module 502 produces an image of an examined eye (not shown) and provides it to the optical fiber unit 506. The optical fiber unit 506 conveys this image and provides it to the image capturing element 504. Thus, the hand-held object is reduced so as not to include the image capturing element 504, thereby making it smaller and more convenient to use.

Figure 6:
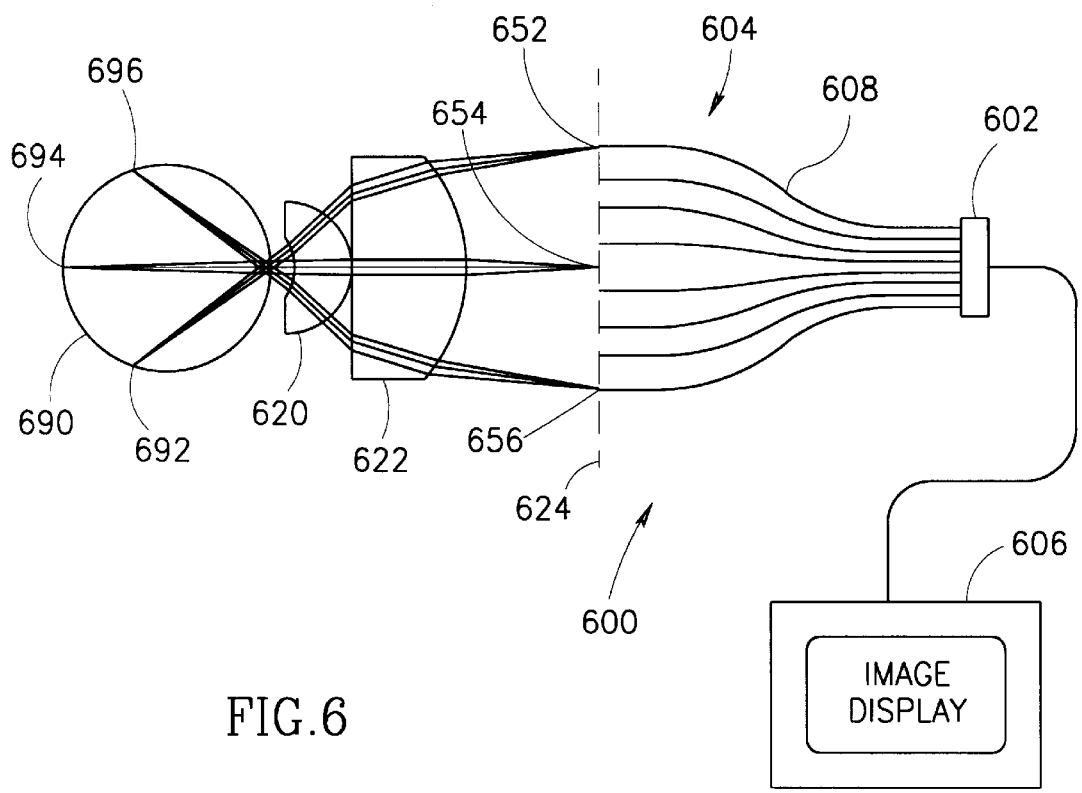
FIG. 6 is a schematic illustration of an apparatus for wide angle examination of the eye, constructed and operative in accordance with yet another preferred embodiment of the invention.

Reference is now made to FIG. 6 which is a schematic illustration of an apparatus for wide angle examination of the eye, generally designated 600, constructed and operative in accordance with yet another preferred embodiment of the invention.

Apparatus 600 includes an optical imaging module 604 and an image capturing element 602, such as charge coupled device (CCD), which is connected to a display apparatus 606. Optical imaging module 604 is brought to close proximity or into contact with an eye 690 to be examined. It is noted that image capturing element 602 can be a photographic camera, a CCD and the like.

The optical imaging module 604 includes an optic fiber CCD coupler 608 and a plurality of lenses 620 and 622 which form a front optical complex which generates a first image of the eye reticulum on a plane 624. Points 652, 654 and 656 are the images of points 692, 694 and 696 correspondingly. According to the present example, the front optical complex is divided into two lenses by way of convenience, while it will be appreciated that it may be implemented by a single lens or more than two lenses. This front optical complex provides a wide angle view of the eye fundus even through an undiluted, 2 mm wide, pupil.

It will be appreciated that the radius of curvature of the front curved plane of lens 620 is similar to the radius of curvature of the tested eye. According to the invention, lens 620 can be replaced so as to adapt the apparatus 600 to various eye sizes.

Optic fiber CCD coupler 608 is an image minifier CCD coupler such as those manufactured by SCHOTT FIBER OPTICS Ltd. of 122, Charlton st., Southbridge, Mass. USA.

Optic fiber CCD) coupler 608 includes a plurality of optic fibers which are spread over the image plane 624 at one end and are compacted into the image capturing element 602, at their other end. Thus, the size of the image, produced at the image plain 624, is reduced to the size of the image capturing element 602.

The image capturing element 602 then detects this image, transforms it into an electrical signal and provides it to display 606 for display.

It is noted that the illumination units 300, 400 and 450 are operative with and around apparatus 600, for providing efficient illumination of the fundus.

It will be appreciated by persons skilled in the art that the present invention is not limited to what has been particularly shown and described hereinabove. Rather the scope of the present invention is defined only by the claims which follow.

We claim:

1. Apparatus for wide angle examination of the eye fundus comprising:

an optical module providing a wide angle view image of said eye fundus, an image capturing unit connected to said optical module for capturing said wide angle view image, and an illuminating unit surrounding said optical module, being disposed, during operation, in the vicinity of the eye, for illuminating said eye directly through the eye globe, said illuminating unit comprising a light source connected to a plurality of light guiding elements, said light guiding elements forming a hollow cylinder, said light guiding elements being curved at a distal end so as to adapt to the curved surface of the examined eye.

2. Apparatus according to claim 1 wherein said image capturing unit is selected from the group consisting of:
   a photographic camera;
   a video camera; and
   a CCD.

3. Apparatus according to claim 1 wherein said optical module comprises:
   a front lens complex for providing a primary large scale image of said fundus; and
   an optical relay, connected to said front lens complex, for transforming said primary large scale image into a small scale image.

4. Apparatus according to claim 3 further comprising an aberration correction optical complex, connected to said optical relay, for correcting color aberration and straightening curvature of said small scale image.

5. Apparatus according to claim 4 further comprising a rear lens complex, connected to said aberration correction optical complex, for imaging said small scale image on a predetermined plain.

6. Apparatus according to claim 1 wherein said indirect illuminating unit further comprises a circumferencial ring connected to the end of each said light guiding elements.

7. Apparatus according to claim 1 wherein said indirect illuminating unit comprises:
   a plurality of light sources, and
   a circumferencial ring, having a tangential cross-section,
   wherein said plurality of light sources being mounted on the periphery of said circumferencial ring.

8. Apparatus for wide angle examination of the eye fundus comprising:
   an optical module providing a wide angle view image of said eye fundus,
   an image capturing unit connected to said optical module for capturing said wide angle view image, said optical module comprising a front lens complex for providing a primary large scale image of said fundus; and
   an optical relay, connected to said front lens complex, for transforming said primary large scale image into a small scale image, said apparatus further comprising an aberration correction optical complex, connected to said optical relay, for correcting color aberration and straightening curvature of said small scale image.

9. Apparatus according to claim 8 further comprising a rear lens complex, connected to said aberration correction optical complex, for imaging said small scale image on a predetermined plain.

10. Apparatus for wide angle examination of the eye fundus comprising:
    an optical module providing a wide angle view image of said eye fundus,
    an image capturing unit connected to said optical module for capturing said wide angle view image, and
    an illuminating unit surrounding said optical module, wherein said illumination unit is a direct illumination unit, for illuminating said eye directly through the pupil.

11. Apparatus for wide angle examination of the eye fundus comprising:
    an optical module providing a wide angle view image of said eye fundus,
    an image capturing unit connected to said optical module for capturing said wide angle view image, and
    an optical fiber unit connected between said optical module and said image capturing unit.

12. Apparatus for wide angle examination of the eye fundus comprising:
    an optical module providing a wide angle view image of said eye fundus, and
    an image capturing unit connected to said optical module for capturing said wide angle view image,
    wherein said optical module comprises:
       a front lens complex for providing a primary large scale image of said fundus; and
       an optic fiber CCD coupler, connected to said front lens complex, for transforming said primary large scale image into a small scale image.

13. Apparatus for wide angle examination of the eye fundus comprising:
    an optical module providing a wide angle view image of said eye fundus,
    an image capturing unit connected to said optical module for capturing said wide angle view image,
    an illuminating unit surrounding said optical module, said illuminating unit comprising a light source connected to a plurality of light guiding elements, and
    a controller connected to said light guiding elements for controlling light intensity, light distribution and restricted light of predetermined wavelengths.

* * * * *